United States Patent [19]
Tsujiyama et al.

[11] Patent Number: 6,015,605
[45] Date of Patent: Jan. 18, 2000

[54] FILAMENT NONWOVEN FABRIC AND ABSORBENT ARTICLE USING THE SAME

[75] Inventors: Yoshimi Tsujiyama; Toshikatsu Fujiwara; Shingo Horiuchi, all of Moriyama, Japan

[73] Assignee: Chisso Corporation, Osaka, Japan

[21] Appl. No.: 09/246,373

[22] Filed: Feb. 8, 1999

Related U.S. Application Data

[63] Continuation of application No. PCT/JP98/02577, Jun. 10, 1998.

[30] Foreign Application Priority Data

Jun. 11, 1997 [JP] Japan ..................................... 9-153901

[51] Int. Cl.$^7$ ...................................................... B32B 3/00
[52] U.S. Cl. .......................... 428/195; 428/219; 428/364
[58] Field of Search ................................... 428/195, 219; 442/364

[56] References Cited

FOREIGN PATENT DOCUMENTS

| | | |
|---|---|---|
| 54-125773 | 9/1979 | Japan . |
| 60-194160 | 10/1985 | Japan . |
| 60-199961 | 10/1985 | Japan . |
| 64-6160 | 1/1989 | Japan . |
| 1-201503 | 8/1989 | Japan . |

*Primary Examiner*—Christopher Raimund
*Attorney, Agent, or Firm*—Merchant & Gould P.C.

[57] ABSTRACT

A filament nonwoven fabric comprising thermoplastic fibers with a fineness of 0.1 to 10 d/f, having a basis weight of 5 to 35 g/m$^2$, and having thermally press bonded portions, in which the conditions (A), (B), and (C) below are satisfied:

(A) the area rate of the thermally press bonded portions being from 5 to 25%;

(B) X≦2.0 (mm)
X: the average value of the distance between adjacent thermally press bonded portions in the mechanical direction of the nonwoven fabric;

Y≦2.5 (mm)
Y: the average value of the distance between adjacent thermally press bonded portions in the direction perpendicular to the mechanical direction of the nonwoven fabric; and (C) the average value of the ratio between the maximum diameters of the thermally press bonded portions satisfying $1 \leq y/x \leq 15$, wherein
x: the average value of the maximum diameter of the thermally press bonded portions in the mechanical direction of the nonwoven fabric; and
y: the average value of the maximum diameter of the thermally press bonded portions in the direction perpendicular to the mechanical direction of the nonwoven fabric.

14 Claims, 4 Drawing Sheets

FILAMENT NONWOVEN FABRIC AND ABSORBENT ARTICLE USING THE SAME

This application is a continuation of PCT/JP98/02577 filed Jun. 10, 1998, pending.

TECHNICAL FIELD

The present invention relates to filament nonwoven fabrics comprising thermoplastic fibers partially thermally press bonded and to absorbent articles using the same. More particularly, the present invention relates to filament nonwoven fabrics excellent in strength, hand feeling, and abrasion resistance, and to absorbent articles using the same.

TECHNICAL BACKGROUND

Conventionally, nonwoven fabrics have been used in various applications such as clothing, industrial materials, materials of construction and architecture, agricultural and horticultural materials, materials of daily needs, medical and sanitary materials, and the like. Particularly, nonwoven fabrics comprising filaments have been widely used, since they have a higher strength compared with nonwoven fabrics comprising staple fibers, and in addition can be provided with excellent productivity. Particularly, nonwoven fabrics partially processed by thermal press bonding have very excellent strength and hand feeling. However, a nonwoven fabric processed by this method partially has non-bonded portions, and fuzz or pilling is likely to be caused in such non-bonded portions due to friction. Because continuous filaments are more subject to resistance due to friction compared with staple fibers, they easily develop fuzz or pilling. Thus, in a filament nonwoven fabric processed by thermal press bonding, it is very difficult to retain a high strength and good hand feeling, while having abrasion resistance.

For examples, Japanese Published Unexamined Patent Application No. (Tokkai Sho) 60-194160 discloses a step of passing a nonwoven fabric through thermal flat rolls so as to provide the nonwoven fabric with a film-like surface, in order to provide abrasion resistance. A nonwoven fabric obtained by this method has good abrasion resistance, but the hand feeling of the nonwoven fabric is deteriorated. Also, Japanese Published Unexamined Patent Application No. (Tokkai Sho) 60-199961 discloses partial press bonding of a nonwoven fabric with an embossing roll, followed by adhering fibers with one another with a hot air circulator. However, in this method, because the heat history of the nonwoven fabric becomes large, the hand feeling of the nonwoven fabric is impaired. Moreover, the processing steps become complicated.

As is described above, a filament nonwoven fabric excellent in all of strength, hand feeling, and abrasion resistance has not yet been obtained.

Thus, the present invention has objects to provide a filament nonwoven fabric excellent in all of strength, hand feeling, and abrasion resistance, and to provide absorbent articles using the same.

SUMMARY OF THE INVENTION

In order to attain the above objects, the present invention provides a nonwoven fabric and an absorbent article using the nonwoven fabric as follows:

(1) A filament nonwoven fabric comprising thermoplastic fibers with a fineness of 0.1 to 10 d/f, having a basis weight of 5 to 35 g/m², and having thermally press bonded portions, in which the conditions (A), (B), and (C) below are satisfied:

(A) the area rate of the thermally press bonded portions being from 5 to 25%;

(B) $X \leq 2.0$ (mm)

X: the average value of the distance between adjacent thermally press bonded portions in the mechanical direction of the nonwoven fabric;

$Y \leq 2.5$ (mm)

Y: the average value of the distance between adjacent thermally press bonded portions in the direction perpendicular to the mechanical direction of the nonwoven fabric; and (C) the average value of the ratio between the maximum diameters of the thermally press bonded portions satisfying $1 \leq y/x \leq 15$, wherein x: the average value of the maximum diameter of the thermally press bonded portions in the mechanical direction of the nonwoven fabric; and y: the average value of the maximum diameter of the thermally press bonded portions in the direction perpendicular to the mechanical direction of the nonwoven fabric.

(2) A filament nonwoven fabric according to the above (1), wherein the fineness of the thermoplastic fibers that constitute the nonwoven fabric is from 0.1 to 6 d/f, and wherein X satisfies (B') $0.3 \leq X \leq 1.6$ (mm).

(3) A filament nonwoven fabric according to the above (1) or (2), wherein the filament nonwoven fabric is one obtained by the spun bond method.

(4) A filament nonwoven fabric according to the above (1) or (2), wherein the thermoplastic fibers are conjugated fibers comprising a high melting core component and a low melting or softening sheath component, the low melting or softening component having a volume ratio of 40 to 90% based on the total volume of the conjugated fibers.

(5) A filament nonwoven fabric according to the above (4), wherein the low melting component of the thermoplastic fibers comprises polyethylene.

(6) A filament nonwoven fabric according to the above (4), wherein the low melting or softening component of the thermoplastic fibers comprises at least one selected from olefin binary copolymers and olefin terpolymers.

(7) A filament nonwoven fabric according to the above (4), wherein the core component of the thermoplastic fibers comprises at least one selected from polypropylene and polyethylene terephthalate.

(8) An absorbent article using a filament nonwoven fabric according to the above (1) or (2) in a part thereof.

DETAILED DESCRIPTION OF THE INVENTION

Figure 1:
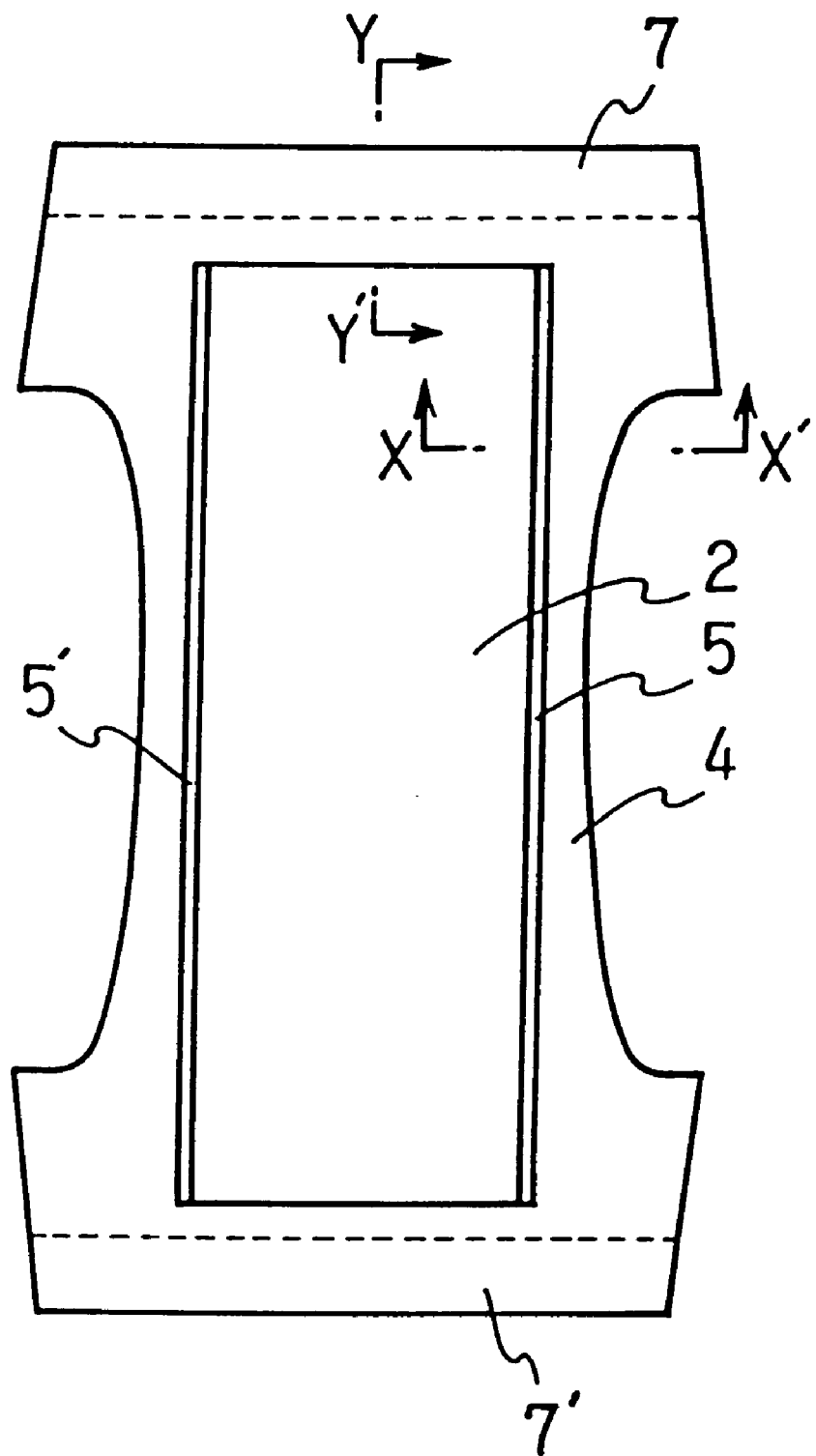
FIG. 1 is a developed plan view of one embodiment of a disposable diaper using the filament nonwoven fabric of the present invention in a part thereof, viewed from the skin side.

The present invention will be described in detail below.

The nonwoven fabric used in the present invention comprises thermoplastic fibers, so that the nonwoven fabric partially can have thermally press bonded portions. As the resin component that constitutes the thermoplastic fibers, polyolefin resins, polyester resins, polyamide resins, or the like are preferably used. Examples of the polyolefin resins include polypropylene, high density polyethylene, intermediate density polyethylene, low density polyethylene, ethylene/propylene copolymer, ethylene/butene-1/propylene terpolymer, and the like. Examples of the polyester resins include polyethylene terephthalate, polybutylene terephthalate, and the like. Examples of the polyamide resins include nylon 6, nylon 66, and the like. Moreover, pigment, flame retardant, deodorant, antistatic agent, antioxidant, or the like may be added to the thermoplastic fibers comprising these resins as needed, as long as it does not inhibit the effects of the present invention.

The filament nonwoven fabric of the present invention can be obtained by melt spinning using the above resins and obtaining thermoplastic fibers through a spinneret. The filament nonwoven fabric can be easily produced by the well-known spun bond method.

To be specific, for example, resins are fed to an extruder and melt spun through a spinneret. A group of fibers discharged from the spinneret is introduced into an air sucker and stretched by drawing, so that a group of filaments is obtained. Then, the group of filaments discharged from the air sucker is electrically charged by applying same charges with an appropriate charging apparatus such as a corona discharge device. Thereafter, it is passed through between a couple of vibrating wing-like tools (flaps), or collided against an appropriate reflection plate, so that the filaments are opened. The opened filaments are collected as a filament fleece on an endless net conveyor having suckers on its back surface.

Furthermore, other than by the above-mentioned spun bond method, the nonwoven fabric used in the present invention may be also produced by opening a tow obtained by general melt spinning.

Furthermore, in producing the filament nonwoven fabric of the present invention, conjugated fibers comprising a low melting or softening resin component and a high melting resin component, wherein the melting or softening point and the melting point of these respective components differ by at least 15° C., may be used. When such conjugated fibers are used, resins for respective components are fed to respective extruders, and melt spun through a composite spinneret.

Still furthermore, the nonwoven fabric of the present invention may comprise combined filament fibers, which comprises filaments comprising a low melting or softening resin component and filaments comprising a high melting resin component, wherein the melting or softening point and the melting point of the respective filaments differ by at least 15° C. Hereinafter, unless specified otherwise, a low melting or softening resin/component may be generally referred to as a low melting resin/component.

The melting points of these resins can be determined as the temperature at the top of the peak of the heat absorption curve obtained by DSC (differential scanning calorimetry) with an increasing temperature of 10° C./min. Moreover, the softening points are measured according to JIS K 2531.

As mentioned above, when the filaments of the nonwoven fabric of the present invention comprises conjugated fibers, the conjugated fibers may have two components, or three or more components, e.g. three or four components. However, two-component conjugated fibers comprising a low melting resin and a high melting resin may be sufficient in view of economy, except for a special use. Furthermore, as such conjugated filaments, various types of conjugated fibers such as core/sheath type, eccentric core/sheath type, side-by-side type, multi-layered type, or island-in-sea type may be used. In this case, it is preferable that at least the low melting component is exposed on the surface of the conjugated fibers along the longitudinal direction.

The cross-sectional shape of the fibers used in the filament nonwoven fabric of the present invention may be circular, or various different shapes such as triangular or compressed (noncircular cross section). It also may be a hollow cross section. Moreover, a combination of two or more different types of these fibers also may be used.

It is necessary that the fineness of the fibers that constitutes the filament nonwoven fabric of the present invention is from 0.1 to 10 d/f, preferably from 0.1 to 6 d/f. If the fineness is smaller than 0.1 d/f, the cost increases, and fuzz is likely to be developed. Moreover, if the fineness is greater than 10 d/f, hand feeling is undesirably reduced.

Furthermore, it is necessary that the basis weight of the filament nonwoven fabric of the present invention is in the range of 5 to 35 g/m$^2$. If the basis weight is smaller than 5 g/m$^2$, a nonwoven fabric with a low strength is undesirably obtained. Moreover, if the basis weight is greater than 35 g/m$^2$, a nonwoven fabric with poor hand feeling is undesirably obtained. The basis weight herein means the weight (g) of a nonwoven fabric per square meter.

The filament nonwoven fabric of the present invention has thermally press bonded portions. The thermally press bonded portions are where the shapes of fibers are modified compared with portions not thermally press bonded, and where fibers are adhered to one another. And the partial thermal press bonding of the nonwoven fabric is performed in order to increase the strength of the nonwoven fabric. The shape of the thermally press bonded portions may be circular, elliptic, or polygonal, but is not particularly limited.

However, it is necessary that the filament nonwoven fabric of the present invention satisfies the conditions (A), (B), and (C) as follows:

(A) the area rate of the thermally press bonded portions being 5 to 25%;

(B) $X \leq 2.0$ (mm)

X: the average value of the distance between adjacent thermally press bonded portions in the mechanical direction of the nonwoven fabric;

$Y \leq 2.5$ (mm)

Y: the average value of the distance between adjacent thermally press bonded portions in the direction perpendicular to the mechanical direction of the nonwoven fabric; and (C) the average value of the ratio between the maximum diameters of the thermally press bonded portions satisfying $1 \leq y/x \leq 15$, wherein x: the average value of the maximum diameter of the thermally press bonded portions in the mechanical direction of the nonwoven fabric; and y: the average value of the maximum diameter of the thermally press bonded portions in the direction perpendicular to the mechanical direction of the nonwoven fabric.

The above-mentioned area rate of the thermally press bonded portions means the percentage of the area of the thermally press bonded portions included in a unit area of the nonwoven fabric. When the unit area of the nonwoven fabric is F mm$^2$, and the area of the thermally press bonded portions included in the unit area is G mm$^2$, the area rate (%) of the thermally press bonded portions can be shown by (G/F)×100 (%). For example, when the total area of the thermally press bonded portions is 10 mm$^2$ in a nonwoven fabric having a size of 10 mm×10 mm, the area rate (%) of the thermally press bonded portions is 10%. The measurement is usually performed with an electron microscope or the like in a unit area of 10 mm×10 mm of the nonwoven fabric. It is preferable to include other portions having the same unit area in the nonwoven fabric so that a total of ten portions of the unit area are measured, and the average value thereof is determined.

In the nonwoven fabric of the present invention, it is necessary that the area rate of the thermally press bonded portions is from 5 to 25%. If the area rate exceeds 25%, since the thermally press bonded portions are film-like, freeness of fibers is lost. Thus, a nonwoven fabric having poor hand feeling is undesirably obtained.

Also, if the area rate of the thermally press bonded portions is less than 5%, a nonwoven fabric with a low strength is undesirably obtained.

Furthermore, in the filament nonwoven fabric of the present invention, it is necessary that the average value X of the distance between adjacent thermally press bonded portions in the mechanical direction of the nonwoven fabric is 2.0 mm or less, and the average value Y of the distance between adjacent thermally press bonded portions in the direction perpendicular to the mechanical direction of the nonwoven fabric is 2.5 mm or less.

The mechanical direction of a nonwoven fabric means the direction in which the nonwoven fabric is moved through an apparatus for producing the nonwoven fabric in the production process. Fibers that constitute a nonwoven fabric usually tend to be oriented mainly in the mechanical direction of the nonwoven fabric.

Figure 6:
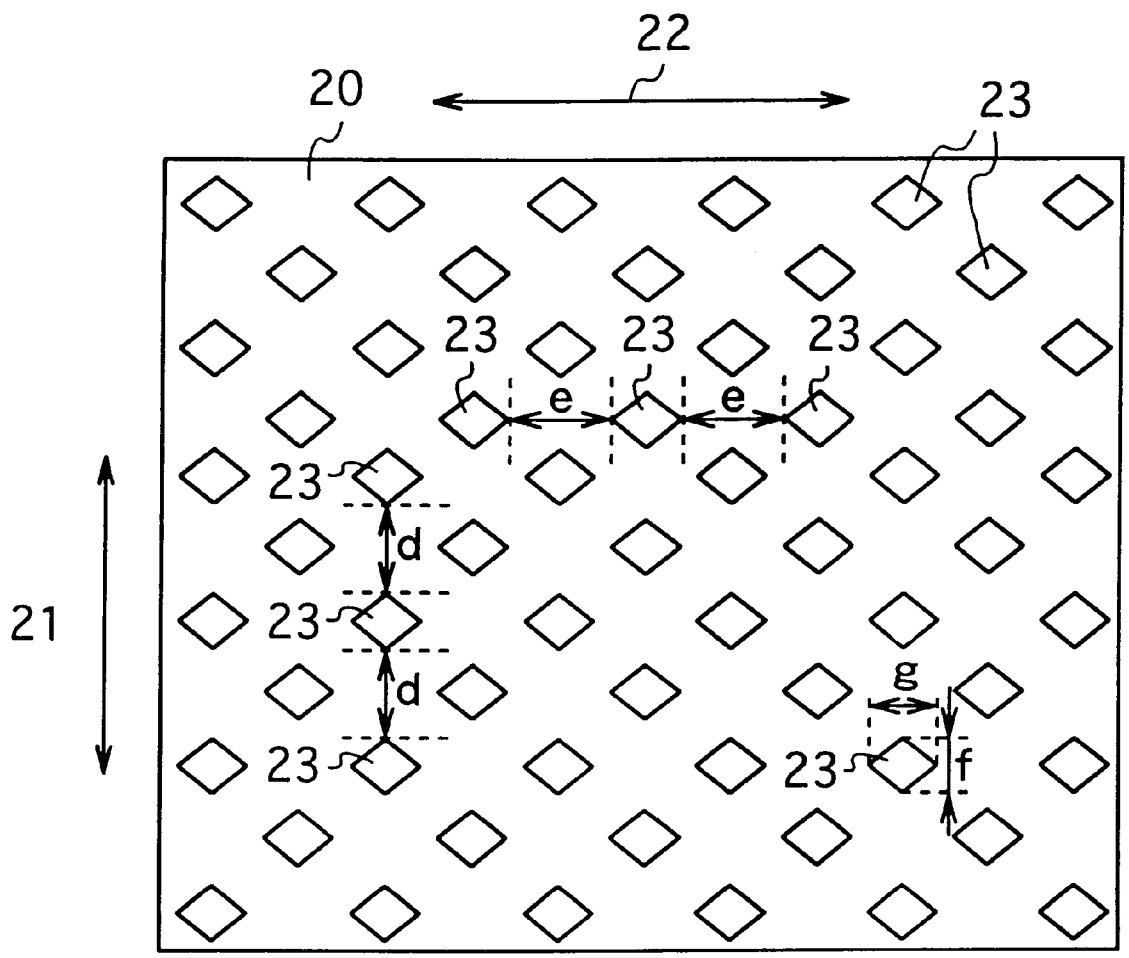
FIG. 6 is a plan view of one embodiment of the filament nonwoven fabric of the present invention, for explaining X, Y, x, and y in the conditions (A), (B), and (C) for the filament nonwoven fabric of the present invention.

Referring, for example, to the plan view of a nonwoven fabric shown in FIG. 6, the distance between adjacent thermally press bonded portions in the mechanical direction of the nonwoven fabric will be explained below. When thermally press bonded portions 23 of a filament nonwoven fabric 20 have shapes as illustrated in FIG. 6, the distances between adjacent thermally press bonded portions in the mechanical direction of the nonwoven fabric are the distances (d) between adjacent portions 23, the mechanical direction of the filament nonwoven fabric 20 being the direction according to an arrow 21, and the direction perpendicular to the mechanical direction being the direction according to an arrow 22. The distances usually are measured with an electron microscope or the like in a unit area of 10 mm×10 mm of the nonwoven fabric. Including other portions having the same unit area in the nonwoven fabric, a total of ten portions of the unit area are measured, and the average value thereof is determined as X (mm).

When the thermally press bonded portions of the nonwoven fabric have shapes as shown in FIG. 6, the distances between adjacent thermally press bonded portions in the direction perpendicular to the mechanical direction of the nonwoven fabric are the distances (e) between adjacent thermally press bonded portions 23 in the direction perpendicular to the mechanical direction of the nonwoven fabric (the direction according to the arrow 22). The distances usually are measured with an electron microscope or the like in a unit area of 10 mm×10 mm of the nonwoven fabric. Including other portions having the same unit area in the nonwoven fabric, a total of ten portions of the unit area are measured, and the average value thereof is determined as Y (mm).

When the thermally press bonded portions are firmly adhered, free fibers in portions not thermally press bonded are stretched by abrasion resistance, and the stretched fibers become the cause of fuzz or pilling. Moreover, even if the thermally press bonded portions are firmly adhered, if abrasion resistance applied per one fiber is large, fibers are peeled off from the thermally press bonded portions, thus causing fuzz or pilling. In any case, the smaller the length of the fibers in the portions not thermally press bonded, the better the abrasion resistance. That is, the smaller the distance between adjacent thermally press bonded portions, the better the abrasion resistance. If X is larger than 2.0 mm, or Y is larger than 2.5 mm, the abrasion resistance becomes poor. Further preferably, X is at least 0.3 mm, but not more than 1.6 mm. Moreover, Y is preferably at least 0.3 mm.

A filament nonwoven fabric typically produced by the spun bond method is more likely to develop fuzz or pilling by abrasion in the direction perpendicular to the mechanical direction of the nonwoven fabric, than by that in the direction parallel to the mechanical direction of the nonwoven fabric. Therefore, fuzz or pilling is likely to be developed when X is large. Therefore, X is preferably not more than 1.6 mm. Moreover, although not particularly limited, in order to maintain good hand feeling of the nonwoven fabric, it is preferable that both X and Y are at least 0.3 mm.

In the present invention, there is a tendency that the abrasion resistance is more improved as the area of each thermally press bonded portion is increased. However, the hand feeling of the nonwoven fabric is more deteriorated as the area of each thermally press bonded portion is increased. Therefore, it is preferable to consider avoiding a decrease in abrasion resistance by making the area of each thermally press bonded portion as small as possible.

Fibers in a filament nonwoven fabric typically produced by the spun bond method tend to be aligned in the mechanical direction of the nonwoven fabric. Therefore, fuzz or pilling is likely to be developed by abrasion in the direction perpendicular to the mechanical direction of the nonwoven fabric. In order to improve the abrasion resistance in the direction perpendicular to the mechanical direction of the nonwoven fabric, many fibers should be fixed at each thermally press bonded portion. When the thermally press bonded portions have shapes longer in the direction perpendicular to the mechanical direction of the nonwoven fabric, the area of each thermally press bonded portion becomes small while many fibers are bonded, so that good balance between hand feeling and abrasion resistance can be obtained. Thus, it is necessary that the average value of the ratio between the maximum diameters of the thermally press bonded portions (i.e. the average value (y) of the maximum diameters of the thermally press bonded portions in the direction perpendicular to the mechanical direction of the nonwoven fabric/the average value (x) of the maximum diameters of the thermally press bonded portions in the mechanical direction of the nonwoven fabric) is not less than 1 but not more than 15, preferably in the range of 1.2 to 5.

For example, when the thermally press bonded portions have shapes as shown in FIG. 6, the maximum diameter of the thermally press bonded portions in the mechanical direction of the nonwoven fabric is the length shown by (f), and the maximum diameter of the thermally press bonded portions in the direction perpendicular to the mechanical direction of the nonwoven fabric is the length shown by (g). These lengths are usually measured with an electron microscope or the like in a unit area of 10 mm×10 mm of the nonwoven fabric. Including other portions of the same unit area in the nonwoven fabric, a total of ten portions of the unit area are measured, and the average values thereof are determined as x (mm) and y (mm), respectively.

If the average value of the ratio between the maximum diameters of the thermally press bonded portions is less than 1, abrasion resistance becomes undesirably poor. If the average value of the ratio between the maximum diameters of the thermally press bonded portions is greater than 15, hand feeling in the direction perpendicular to the mechanical direction of the nonwoven fabric becomes undesirably poor.

The method of forming thermally press bonded portions that satisfy the above conditions (A), (B), and (C) in the filament nonwoven fabric is not particularly limited, and any method can be employed as long as the conditions (A), (B), and (C) are satisfied. For example, thermally press bonded portions may be formed in the filament nonwoven fabric with a point bond processor comprising heated embossing roll and smooth surface roll. The thermally press bonded portions are produced by the convex portions of the embossing roll as the nonwoven fabric is passed through between the two rolls of the point bond processor. In this case, for example, the embossing roll has been processed to have convex portions with shapes, sizes, number, positions and spaces so as to produce thermally press bonded portions that satisfy the above conditions (A), (B), and (C).

It is preferable that the filament nonwoven fabric of the present invention comprises conjugated fibers having a high melting core component and a low melting or softening sheath component. In this case, the nonwoven fabric can be processed by thermal press bonding at a temperature near the melting or softening point of the sheath component that lies on the surface of fibers. Thus, the damage to the core component of the fibers by heat can be reduced, and a nonwoven fabric with good hand feeling can be obtained. In the above-mentioned conjugated fibers, as the proportion of the sheath component is increased, the thermally press bonded portions are more firmly fixed and abrasion resistance is more improved. Thus, the volume ratio between the sheath component and the core component (the ratio of sheath/core) is suitably from (4/6) to (9/1).

A nonwoven fabric with good hand feeling can be obtained by using polyethylene for the sheath component, since the thermal press bonding process can be performed at a low temperature and thus the damage to the core component by heat is small. In one preferable embodiment, at least one selected from olefin binary copolymers and olefin terpolymers is used for the sheath component, because these can be easily bonded with other materials such as polypropylene nonwoven fabric or film by thermal bonding.

Examples of olefin binary copolymers and olefin terpolymers include ethylene/propylene copolymer comprising 85 to 99 wt. % of propylene and 1 to 15 wt. % of ethylene; butene/propylene copolymer comprising 50 to 99 wt. % of propylene and 1 to 50 wt. % of 1-butene; ethylene/octene copolymer comprising 73 to 99 wt. % of ethylene and 1 to 27 wt. % of 1-octene (more preferably ethylene/octene copolymer comprising 75 to 98 wt. % of ethylene and 2 to 25 wt. % of 1-octene); ethylene/butene/propylene copolymer comprising 84 to 98 wt. % of propylene, 1 to 15 wt. % of 1-butene, and 1 to 15 wt. % of ethylene; and the like. However, it should be noted that these are non-limiting examples.

When conjugated fibers are used, polypropylene is preferably used for the core component, since a relatively soft nonwoven fabric can be obtained. Also, polyethylene terephthalate is preferably used for the core component, because a filament nonwoven fabric with a higher strength, which exhibits more excellent elasticity (cushion property) when crimp is developed, can be obtained.

The filament nonwoven fabric of the present invention may be used either alone or as a laminate with other materials such as staple fiber nonwoven fabrics, melt-blown nonwoven fabrics, or films.

The obtained filament nonwoven fabric of the present invention is excellent in abrasion resistance, strength, and hand feeling, and may be used in various applications. Particularly, it is suitably used in absorbent articles such as sanitary napkins and disposable diapers.

The absorbent articles such as disposable diapers, sanitary napkins and the like have structures in that body fluids such as urine, blood or the like are absorbed and leakage is prevented. The structure of such absorbent articles may differ somewhat between respective embodiments. However, such an absorbent article comprises at least a liquid absorption layer for absorbing and retaining body fluids such as urine, blood or the like; a liquid permeable front cover sheet comprising, for example, a nonwoven fabric and located at the side of the front surface (the side contacting with the user's skin); and a liquid impermeable back sheet located at the back side that prevents the absorbed body fluids from leaking outside. Moreover, in general, in absorbent articles such as disposable diapers or sanitary napkins, in addition to the back sheet, water repellent side sheets comprising, for example, a nonwoven fabric is provided at both sides of the absorbent articles so as to prevent absorbed liquid such as body fluids from leaking, in case that the absorbent articles are displaced from the desired place due to the user's physical motion or as a user lays down on his/her side. (In the case of disposable diapers or the like, since the water repellent side sheets are often provided with gathers, they also are called a side gather or a leg cuff etc. In the case of disposable diapers, such side sheets are provided in a place that holds the joints of the thigh or the circumference of the thigh.) In addition, in disposable diapers, a water-repellent round sheet which comprises a nonwoven fabric or the like is also provided at the skin side of the portion covering the abdomen or of the portion covering the upper buttock located opposite to the abdomen. The water repellent round sheet is provided to prevent liquids such as body fluids or the like which are absorbed by the absorbent articles from leaking outside of the absorbent articles, in case that the liquids leak to the abdomen or the upper buttock portion as the user falls down or lays down or turns the body. Moreover, in the case of disposable diapers or the like, belt-like waist gather sheets etc. may be provided at the skin side of the waist portion. Such sheets also comprise a water repellent sheet comprising, for example, a nonwoven fabric.

Moreover, for the liquid absorption layer, various kinds of appropriate liquid absorption layers are applied. Such a liquid absorption layer comprises, for example, a compressed mixture prepared by mixing an aggregate of fibers comprising cellulose type fibers such as fluff pulp, to which if necessary synthetic fibers are further mixed, with high water absorptive resin, and compressing and hardening the mixture. This liquid absorption layer is, in general, wrapped up by tissue paper or the like. Moreover, for the back sheet, a thermoplastic film is usually used. The thermoplastic film generally has a large number of minute micropores so as to prevent stuffiness inside when worn and to provide ventilation. Moreover, from the viewpoint of improving the plastic-like touch and appearance peculiar to films, or from the viewpoint of improving the strength, a composite comprising a film and a nonwoven fabric also may be used. In addition, there are absorbent articles having more layers, in which additional sheets are inserted so as to provide various kinds of functions.

The above-mentioned filament nonwoven fabric of the present invention can be used for the front cover sheet, side sheets, round sheet, a part of the back sheet (e.g. a laminate with a liquid impermeable sheet), or the like in the absorbent articles depending on the respective objects. Moreover, these respective members are appropriately thermally bonded and fixed with each other at necessary portions.

Moreover, for the bonding between these members by means of thermal press or thermo-compression bonding, partial point bonding which enables bonding at many points usually is preferably employed, although it depends on the portion to be applied.

Hereinafter, the parts of the absorbent article in which the filament nonwoven fabric of the present invention can be used will be explained by showing typical examples with reference to the drawings. However, the structure of the absorbent articles illustrated is just one embodiment, and the absorbent articles are not limited to those having the structures shown in the drawings.

Figure 2:
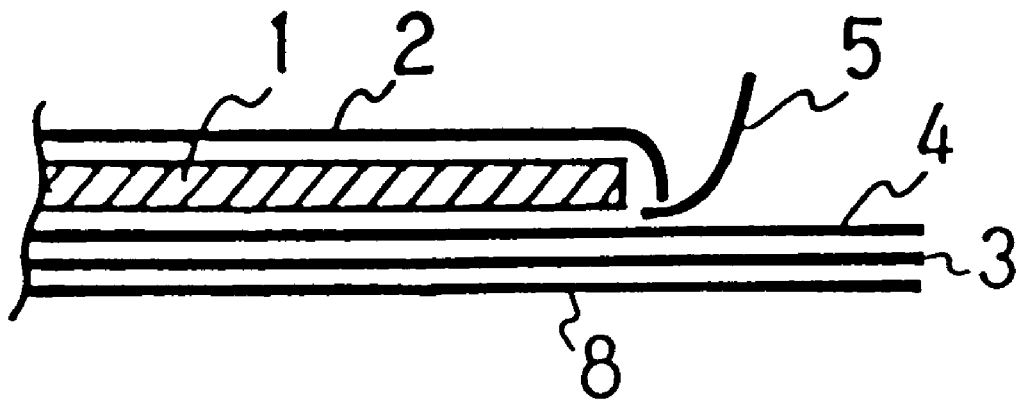
FIG. 2 is a schematic end view of a cross section taken on line X-X' of FIG. 1.

FIG. 1 is a developed plan view showing one embodiment of a disposable diaper when viewed from the side of the user's skin; FIG. 2 is a schematic end view of a cross section taken on line X-X' of FIG. 1; and FIG. 3 is a schematic end view of a cross section taken on line Y-Y' of FIG. 1.

Figure 3:
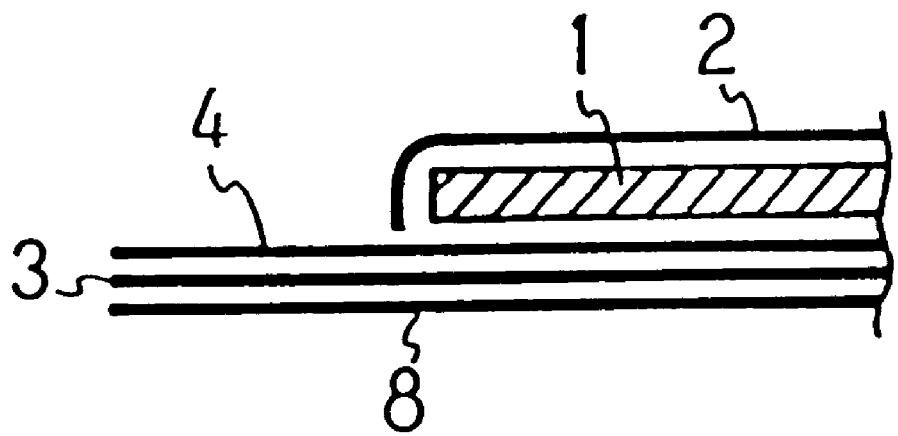
FIG. 3 is a schematic end view of a cross section taken on line Y-Y' of FIG. 1.

In FIGS. 1 to 3, numeral 1 denotes a liquid absorption layer for absorbing and retaining body fluids. Although not particularly limited, it comprises, for example, the compressed mixture in which cellulose type fiber such as fluff pulp, high water absorptive resin, and, if necessary, a mixture of synthetic fibers are mixed, and compressed and hardened. Moreover, the liquid absorption layer 1 is wrapped up by tissue paper (not shown) or the like. Numeral 2 denotes a liquid permeable front cover sheet that is located at the front surface side thereof (the side contacting with the user's skin). The filament nonwoven fabric of the present invention also can be used for this front cover sheet 2. Numeral 3 denotes a back sheet that requires liquid impermeability. On the backside surface of the back sheet 3, the filament nonwoven fabric of the present invention can be laminated as a back sheet laminate 8. By using the filament nonwoven fabric of the present invention as a laminate on the back sheet of such an absorbent article, the cool touch of plastic film and an appearance peculiar to plastics are improved, and warm cloth-like touch and appearance can be provided, while the back sheet can be reinforced. Moreover, when the filament nonwoven fabric of the present invention is used as a laminate, fuzz or pilling is hardly developed, and thus it is preferable.

Although a round sheet 4 is not always necessary, in the examples shown in FIG. 2 and FIG. 3, a round sheet 4 is located between the liquid absorption layer 1 and the back sheet 3. The filament nonwoven fabric of the present invention also can be used for the round sheet 4. And numerals 5 and 5' denote side sheets, which are provided at both sides of the absorbent articles, so as to prevent absorbed liquid such as body fluids from leaking in case that the absorbent articles are displaced from the desired place due to the user's physical motion or as the user lays down on his/her side, as mentioned above. (In the case of disposable diapers, since the side sheets are often provided with gathers, they are also called a side gather or a leg cuff etc. In the case of disposable diapers, such side sheets are provided in a place that holds the joints of the thigh or the circumference of the thigh.) For this side sheet, the filament nonwoven fabric of the present invention also can be used. Moreover, although not particularly shown in FIG. 2 and FIG. 3, as shown in numeral 7 in FIG. 1, a belt like waist gather or the like may be provided at the skin side of the waist portion. The filament nonwoven fabric of the present invention also can be used for the waist gather.

Each of these members is designed so as not to drop off by bonding at appropriate portions with a hot melt adhesive etc., or by means of thermal bonding or ultrasonic bonding without using adhesives (not shown in the drawings).

Moreover, in disposable diapers, the filament nonwoven fabric of the present invention need not be used in every member explained above, and may be used in one or more members.

Figure 4:
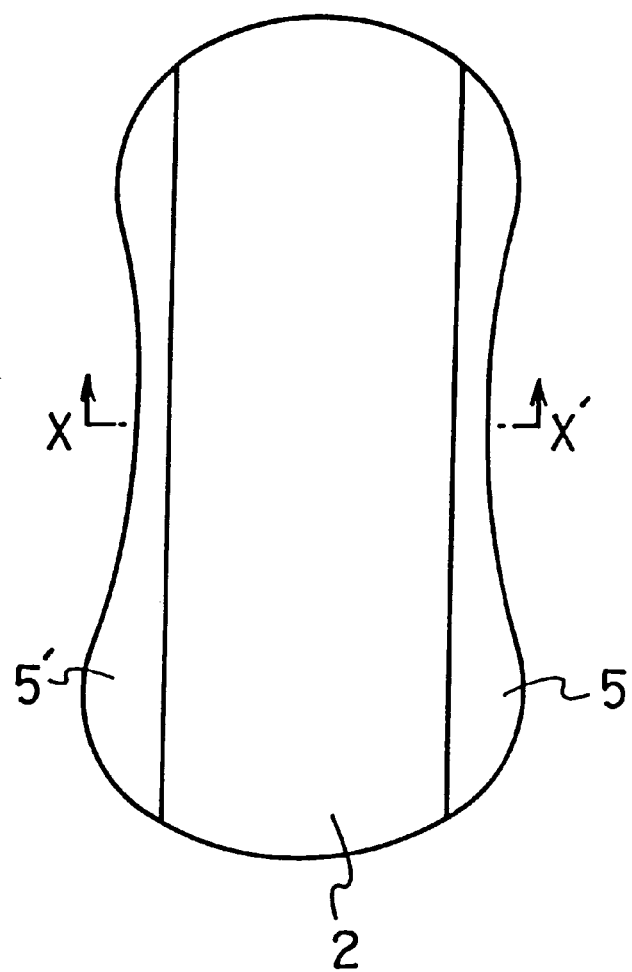
FIG. 4 is a developed plan view of one embodiment of a sanitary napkin using the filament nonwoven fabric of the present invention in a part thereof, viewed from the skin side.
Figure 5:
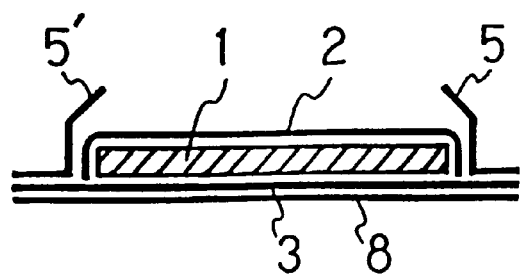
FIG. 5 is a schematic end view of a cross section taken on line X-X' of FIG. 4.

Next, FIG. 4 is a developed plan view showing one embodiment of a sanitary napkin, when viewed from the skin side. FIG. 5 shows a schematic end view of a cross section taken on line X—X' of FIG. 4. Numeral 1 denotes a liquid absorption layer wrapped up by tissue paper (not shown); numeral 2 denotes a liquid permeable front cover sheet lying on the front side surface of the layer 1 (the side contacting with the user's skin; numeral 3 denotes a back sheet that requires liquid impermeability; and numerals 5 and 5' denote side sheets. On the backside of the back sheet 3, the filament nonwoven fabric of the present invention can be laminated as a back sheet laminate 8. Moreover, the filament nonwoven fabric of the present invention also can be used for the side sheets 5 and 5'.

Each of these members is designed so as not to drop off by bonding at appropriate portions with a hot melt adhesive etc., or by means of thermal bonding or ultrasonic bonding without using adhesives (not shown in the drawings).

Needless to say, in the same way as the above, in the absorbent articles, the filament nonwoven fabric of the present invention need not be used in every member explained above, and may be used in one or more members.

The absorbent articles using the filament nonwoven fabric of the present invention therein are excellent in abrasion resistance, strength, and hand feeling.

Best Mode for Carrying Out the Invention

Hereinafter, the present invention will be described in detail by way of examples and comparative examples. However, the present invention should not be construed as limited to these examples.

The measuring methods and evaluation criteria for respective evaluation items are as follows:

Tensile Strength: Tensile test was carried out according to JIS L 1096, and the tensile strengths in the longitudinal direction and the lateral direction were measured. The measured values were divided by the basis weight and the width of the sample, and the obtained values were determined as the tensile strengths in the longitudinal direction and in the lateral direction, respectively. Then, these values were substituted in the formula (the tensile strength in the longitudinal direction X the tensile strength in the lateral direction)$^{1/2}$, and calculated as the tensile strength. The longitudinal direction herein refers to the direction in which a filament nonwoven fabric is carried by an endless conveyor in the process of producing the nonwoven fabric, namely, the mechanical direction. The lateral direction refers to the direction perpendicular to the mechanical direction. Although the unit is shown as kg/cm (g/m$^2$), the (g/m$^2$) in the parenthesis means that it is a reduced value per the unit basis weight of the nonwoven fabric.

Hand Feeling: Sensory test by touching the surface of a filament nonwoven fabric was performed by ten monitors. If a monitor feels good hand touch, one point was added per one person.

Abrasion Resistance: According to JIS L 0849, a filament nonwoven fabric was subjected to reciprocating rubbing at a rate of once per second for one hundred times with Rubbing-Meter FR-2 manufactured by SUGA SHIKENKI Ind., and the result was evaluated by visual determination. One that did not develop fuzz was determined as good (○), and one that developed fuzz was determined as defective (X).

EXAMPLE 1

Polypropylene having a MFR (melt flow rate: the condition 14 in Table 1 of JIS K 7210) of 50 and a melting point of 160° C. was extruded from two 60 mmφ extruders at an extruding temperature of 220° C. at a rate of 2200 cc/min. A spinneret having circular spinning holes with a hole diameter of 0.35 mm arranged in 550 holes×5 columns in the longitudinal direction of the spinneret was used. A group of fibers discharged from the spinneret was introduced into an air sucker and stretched by drawing, so that a group of filaments was obtained. Then, the group of filaments discharged from the air sucker was electrically charged by applying same electric charges with a corona discharge device. Thereafter, it was passed through between a couple of vibrating wing-like tools (flaps) so as to open the filaments. The opened filament group was collected as a filament fleece on an endless conveyor having suckers on its back surface. The drawing speed of the air sucker was adjusted so that the fineness of the filaments obtained at this time may become 2.0 d/f. The collected filament fleece was carried on the endless conveyor at a moving speed of 60 m/min, and introduced between the rolls, pressurized at 80 kg/cm, of a point bond processor comprising an embossing roll and a smooth surface roll which are heated at 141° C. Thus, a filament nonwoven fabric having a basis weight of 20 g/m$^2$ was obtained.

As shown in Table 1, the thermally press bonded portions of the obtained filament nonwoven fabric satisfied the above-mentioned conditions (A), (B), and (C) of the present invention. According to the evaluation result, the obtained nonwoven fabric had a high tensile strength, good hand feeling, and good abrasion resistance.

The above filament nonwoven fabric was used for a front cover sheet 2 of a disposable diaper. At this time, in order to provide liquid permeability, 0.5 wt. % of a hydrophilic spin finish comprising 50 wt. % of polyethylene glycol dimethyl laurate (molecular weight of 400) and 50 wt. % of polyethylene glycol monolaurate (molecular weight of 500) was adhered to the nonwoven fabric.

When the obtained disposable diaper was worn by a user for testing, fuzz or pilling was not developed, hand feeling was good, and no liquid leaking was observed. Thus, a good absorbent article was obtained.

The above-mentioned disposable diaper comprises the above-mentioned front cover sheet; a liquid absorption layer comprising fluff pulp and high water absorptive resin and wrapped up by tissue paper; side sheets of a polypropylene staple fiber nonwoven fabric; a round sheet of a polypropylene staple fiber nonwoven fabric; and a back sheet of a linear low density polyethylene film.

EXAMPLE 2

Polypropylene having a MFR of 50 and a melting point of 160° C. was extruded from two 60 mmφ extruders with an extruding temperature of 220° C. at a rate of 2200 cc/min. A spinneret having circular spinning holes with a hole diameter of 0.35 mm arranged in 550 holes×5 columns in the longitudinal direction of the spinneret was used. A group of fibers discharged from the spinneret was introduced into an air sucker and stretched by drawing, so that a group of filaments was obtained. Then, the group of filaments discharged from the air sucker was electrically charged by applying same electric charges with a corona discharge device. Thereafter, it was passed through between a couple of vibrating wing-like tools (flaps) so as to open the filaments. The opened filament group was collected as a filament fleece on an endless conveyor having suckers on its back surface. The drawing speed of the air sucker was adjusted so that the fineness of the filaments obtained at this time may become 2.0 d/f. The collected filament fleece was carried on the endless conveyor at a moving speed of 60 m/min, and introduced between the rolls, pressurized at 80 kg/cm, of a point bond processor comprising an embossing roll and a smooth surface roll which are heated at 141° C. Thus, a filament nonwoven fabric having a basis weight of 20 g/m$^2$ was obtained.

As shown in Table 1, the thermally press bonded portions of the obtained filament nonwoven fabric satisfied the above-mentioned conditions (A), (B), and (C) of the present invention. According to the evaluation result, the obtained nonwoven fabric had a high tensile strength, good hand feeling, and good abrasion resistance.

The above filament nonwoven fabric was used for side sheets of a disposable diaper.

When the obtained disposable diaper was worn by a user for testing, fuzz or pilling was not developed, hand feeling was good, and no liquid leaking was observed. Thus, a good absorbent article was obtained.

The above-mentioned disposable diaper comprises a front cover sheet of a polypropylene staple fiber nonwoven fabric; a liquid absorption layer comprising fluff pulp and high water absorptive resin and wrapped up by tissue paper; the above-mentioned side sheets; a round sheet of a polypropylene filament nonwoven fabric; and a back sheet of a linear low density polyethylene film.

EXAMPLE 3

Polypropylene having a MFR of 50 and a melting point of 160° C. was extruded from a 60 mmφ extruder at an extruding temperature of 220° C. On the other hand, a high density polyethylene having a MI (melt index: the condition 4 in Table 1 of JIS K 7210) of 25 and a melting point of 133° C. was extruded from another 60 mmφ extruder at an extruding temperature of 220° C. So as to obtain fibers having a cross section with a volume ratio of 5/5 (core component polypropylene/sheath component polyethylene), these resins were spun through a core/sheath type composite spinneret at 2200 cc/min in total amount. As the spinneret, a spinneret having circular spinning holes with a hole diameter of 0.35 mm arranged in 550 holes×5 columns in the longitudinal direction of the spinneret was used. The spinneret was designed so that the cross section of the fibers obtained may become core/sheath type. A group of fibers discharged from the spinneret was introduced into an air sucker and stretched by drawing, so that a group of filaments was obtained. Then, the group of filaments discharged from the air sucker was electrically charged by applying same electric charges with a corona discharge device. Thereafter, it was passed through between a couple of vibrating wing-like tools (flaps) so as to open the filaments. The opened filament group was collected as a filament fleece on an endless conveyor having suckers on its back surface. The drawing speed of the air sucker was adjusted so that the fineness of the filaments obtained at this time may become 2.5 d/f. The collected filament fleece was carried on the endless conveyor at a moving speed of 50 m/min, and introduced between the rolls, pressurized at 80 kg/cm, of a point bond processor comprising an embossing roll and a smooth surface roll which are heated at 130° C. Thus, a filament nonwoven fabric having a basis weight of 28 g/m² was obtained.

As shown in Table 1, the thermally press bonded portions of the obtained filament nonwoven fabric satisfied the above-mentioned conditions (A), (B), and (C) of the present invention. According to the evaluation result, the obtained nonwoven fabric had a high tensile strength, good hand feeling, and good abrasion resistance.

The above filament nonwoven fabric was used for a round sheet of a disposable diaper.

When the obtained disposable diaper was worn by a user for testing, fuzz or pilling was not developed, hand feeling was good, and no liquid leaking was observed. Thus, a good absorbent article was obtained.

The above-mentioned disposable diaper comprises a front cover sheet of a polypropylene staple fiber nonwoven fabric; a liquid absorption layer comprising fluff pulp and high water absorptive resin and wrapped up by tissue paper; side sheets of a polypropylene filament nonwoven fabric; the above-mentioned round sheet; and a back sheet of a linear low density polyethylene film.

EXAMPLE 4

Polypropylene having a MFR of 50 and a melting point of 160° C. was extruded from a 60 mmφ extruder at an extruding temperature of 220° C. On the other hand, a linear low density polyethylene having a MI of 20 and a melting point of 122° C. was extruded from another 60 mmφ extruder at an extruding temperature of 220° C. So as to obtain fibers having a cross section with a volume ratio of 4/6 (core component polypropylene/sheath component polyethylene), these resins were spun through a core/sheath type composite spinneret at 2200 cc/min in total amount. As the spinneret, a spinneret having circular spinning holes with a hole diameter of 0.35 mm arranged in 550 holes×5 columns in the longitudinal direction of the spinneret was used. The spinneret was designed so that the cross section of the fibers obtained may become core/sheath type. A group of fibers discharged from the spinneret was introduced into an air sucker and stretched by drawing, so that a group of filaments was obtained. Then, the group of filaments discharged from the air sucker was electrically charged by applying same electric charges with a corona discharge device. Thereafter, it was passed through between a couple of vibrating wing-like tools (flaps) so as to open the filaments. The opened filament group was collected as a filament fleece on an endless conveyor having suckers on its back surface. The drawing speed of the air sucker was adjusted so that the fineness of the filaments obtained at this time may become 1.5 d/f. The collected filament fleece was carried on the endless conveyor at a moving speed of 70 m/min, and introduced between the rolls, pressurized at 80 kg/cm, of a point bond processor comprising an embossing roll and a smooth surface roll which are heated at 120° C. Thus, a filament nonwoven fabric having a basis weight of 15 g/m² was obtained.

As shown in Table 1, the thermally press bonded portions of the obtained filament nonwoven fabric satisfied the above-mentioned conditions (A), (B), and (C) of the present invention. According to the evaluation result, the obtained nonwoven fabric had a high tensile strength, good hand feeling, and good abrasion resistance.

The above filament nonwoven fabric was used as a back sheet laminate of a disposable diaper. The back sheet laminate was heat sealed to a linear low density polyethylene film.

When the obtained disposable diaper was worn by a user for testing, fuzz or pilling was not developed, hand feeling was good, and appearance was also good. Thus, a good absorbent article was obtained.

The above-mentioned disposable diaper comprises a front cover sheet of a polypropylene staple fiber nonwoven fabric; a liquid absorption layer comprising fluff pulp and high water absorptive resin and wrapped up by tissue paper; side sheets of a polypropylene filament nonwoven fabric; a round sheet of a polypropylene filament nonwoven fabric; a back sheet of a linear low density polyethylene film; and the above-mentioned back sheet laminate.

EXAMPLE 5

Polypropylene having a MFR of 50 and a melting point of 160° C. was extruded from a 60 mmφ extruder at an extruding temperature of 220° C. On the other hand, a linear low density polyethylene having a MI of 20 and a melting point of 122° C. was extruded from another 60 mmφ extruder at an extruding temperature of 220° C. So as to obtain fibers having a cross section with a volume ratio of 4/6 (core component polypropylene/sheath component polyethylene), these resins were spun through an eccentric core/sheath type composite spinneret at 2200 cc/min in total amount. As the spinneret, a spinneret having circular spinning holes with a hole diameter of 0.35 mm arranged in 550 holes×5 columns in the longitudinal direction of the spinneret was used. The spinneret was designed so that the cross section of the fibers may become eccentric core/sheath type. A group of fibers discharged from the spinneret was introduced into an air sucker and stretched by drawing, so that a group of filaments was obtained. Then, the group of filaments discharged from the air sucker was electrically charged by applying same electric charges with a corona discharge device. Thereafter, it was passed through between a couple of vibrating wing-like tools (flaps) so as to open the filaments. The opened filament group was collected as a filament fleece on an endless conveyor having suckers on its back surface. The drawing speed of the air sucker was adjusted so that the fineness of the filaments obtained at this time may become 3.0 d/f. The collected filament fleece was carried on the endless conveyor at a moving speed of 55 m/min, and introduced between the rolls, pressurized at 80 kg/cm, of a point bond processor comprising an embossing roll and a smooth surface roll which are heated at 120° C. Thus, a filament nonwoven fabric having a basis weight of 25 g/m² was obtained.

As shown in Table 1, the thermally press bonded portions of the obtained filament nonwoven fabric satisfied the above-mentioned conditions (A), (B), and (C) of the present invention. According to the evaluation result, the obtained nonwoven fabric had a high tensile strength, good hand feeling, and good abrasion resistance.

The above filament nonwoven fabric was used for a waist gather of a disposable diaper.

When the obtained disposable diaper was worn by a user for testing, fuzz or pilling was not developed, hand feeling was good, and no liquid leaking was observed. Thus, a good absorbent article was obtained.

The above-mentioned disposable diaper comprises a front cover sheet of a polypropylene staple fiber nonwoven fabric; a liquid absorption layer comprising fluff pulp and high water absorptive resin and wrapped up by tissue paper; side sheets of a polypropylene filament nonwoven fabric; a round sheet of a polypropylene filament nonwoven fabric; a back sheet of a linear low density polyethylene film; and the above-mentioned waist gather.

EXAMPLE 6

Polyethylene terephthalate having an IV (intrinsic viscosity) of 0.64 and a melting point of 257° C. was extruded from a 60 mm$\phi$ extruder at an extruding temperature of 320° C. The IV value was measured using a mixture comprising equal weights of phenol and ethane tetrachloride as a solvent at a temperature of 20° C. On the other hand, a linear low density polyethylene having a MI of 20 and a melting point of 122° C. was extruded from another 60 mm$\phi$ extruder at an extruding temperature of 220° C. So as to obtain fibers having a cross section with a volume ratio of 5/5 (core component polyethylene terephthalate/sheath component polyethylene), these resins were spun through a core/sheath type composite spinneret at 2200 cc/min in total amount. As the spinneret, a spinneret having circular spinning holes with a hole diameter of 0.35 mm arranged in 550 holes×5 columns in the longitudinal direction of the spinneret was used. The spinneret was designed so that the cross section of the fibers may become core/sheath type. A group of fibers discharged from the spinneret was introduced into an air sucker and stretched by drawing, so that a group of filaments was obtained. Then, the group of filaments discharged from the air sucker was electrically charged by applying same electric charges with a corona discharge device. Thereafter, it was passed through between a couple of vibrating wing-like tools (flaps) so as to open the filaments. The opened filament group was collected as a filament fleece on an endless conveyor having suckers on its back surface. The drawing speed of the air sucker was adjusted so that the fineness of the filaments obtained at this time may become 2.7 d/f. The collected filament fleece was carried on the endless conveyor at a moving speed of 50 m/min, and introduced between the rolls, pressurized at 80 kg/cm, of a point bond processor comprising an embossing roll and a smooth surface roll which are heated at 120° C. Thus, a filament nonwoven fabric having a basis weight of 28g/m$^2$ was obtained.

As shown in Table 1, the thermally press bonded portions of the obtained filament nonwoven fabric satisfied the above-mentioned conditions (A), (B), and (C) of the present invention. According to the evaluation result, the obtained nonwoven fabric had a high tensile strength, good hand feeling, and good abrasion resistance.

The above filament nonwoven fabric was used for a front cover sheet of a sanitary napkin. At this time, in order to provide liquid permeability, 0.5 wt. % of a hydrophilic spin finish comprising 50 wt. % of polyethylene glycol dimethyl laurate (molecular weight of 400) and 50 wt. % of polyethylene glycol monolaurate (molecular weight of 500) was adhered to the nonwoven fabric.

When the obtained sanitary napkin was worn by a user for testing, fuzz or pilling was not developed, hand feeling was good, and no liquid leaking was observed. Thus, a good absorbent article was obtained.

The above-mentioned sanitary napkin comprises the above-mentioned front cover sheet; a liquid absorption layer comprising fluff pulp and high water absorptive resin and wrapped up by tissue paper; side sheets of a polypropylene filament nonwoven fabric; and a back sheet of a linear low density polyethylene film.

EXAMPLE 7

Polypropylene having a MFR of 50 and a melting point of 160° C. was extruded from a 60 mm$\phi$ extruder at an extruding temperature of 220° C. On the other hand, a propylene/ethylene copolymer (ethylene copolymerization rate of 6 wt. %) having a MFR of 20 and a melting point of 133° C. was extruded from another 60 mm$\phi$ extruder at an extruding temperature of 260° C. So as to obtain fibers having a cross section with a volume ratio of 4/6 (core component polypropylene/sheath component propylene/ethylene copolymer), these resins were spun through a core/sheath type composite spinneret at 2200 cc/min in total amount. As the spinneret, a spinneret having circular spinning holes with a hole diameter of 0.35 mm arranged in 550 holes×5 columns in the longitudinal direction of the spinneret was used. The spinneret was designed so that the cross section of the fibers obtained may become core/sheath type. A group of fibers discharged from the spinneret was introduced into an air sucker and stretched by drawing, so that a group of filaments was obtained. Then, the group of filaments discharged from the air sucker was electrically charged by applying same electric charges with a corona discharge device. Thereafter, it was passed through between a couple of vibrating wing-like tools (flaps) so as to open the filaments. The opened filament group was collected as a filament fleece on an endless conveyor having suckers on its back surface.

The drawing speed of the air sucker was adjusted so that the fineness of the filaments obtained at this time may become 3.0 d/f. The collected filament fleece was carried on the endless conveyor at a moving speed of 60 m/min, and introduced between the rolls, pressurized at 80 kg/cm, of a point bond processor comprising an embossing roll and a smooth surface roll which are heated at 125° C. Thus, a filament nonwoven fabric having a basis weight of 21 g/m$^2$ was obtained.

As shown in Table 1, the thermally press bonded portions of the obtained filament nonwoven fabric satisfied the above-mentioned conditions (A), (B), and (C) of the present invention. According to the evaluation result, the obtained nonwoven fabric had a high tensile strength, good hand feeling, and good abrasion resistance.

The above filament nonwoven fabric was used for side sheets of a sanitary napkin.

When the obtained sanitary napkin was worn by a user for testing, fuzz or pilling was not developed, hand feeling was good, and no liquid leaking was observed. Thus, a good absorbent article was obtained.

Furthermore, the above-mentioned sanitary napkin comprises a front cover sheet of a polypropylene staple fiber nonwoven fabric; a liquid absorption layer comprising fluff pulp and high water absorptive resin and wrapped up by tissue paper; the above-mentioned side sheets; and a back sheet of a linear low density polyethylene film.

COMPARATIVE EXAMPLE 1

Polypropylene having a MFR of 50 and a melting point of 160° C. was extruded from two 60 mmφ extruders at an extruding temperature of 220° C. at a rate of 2200 cc/min. A spinneret having circular spinning holes with a hole diameter of 0.35 mm arranged in 550 holes×5 columns in the longitudinal direction of the spinneret was used. A group of fibers discharged from the spinneret was introduced into an air sucker and stretched by drawing, so that a group of filaments was obtained. Then, the group of filaments discharged from the air sucker was electrically charged by applying same electric charges with a corona discharge device. Thereafter, it was passed through between a couple of vibrating wing-like tools (flaps) so as to open the filaments. The opened filament group was collected as a filament fleece on an endless conveyor having suckers on its back surface. The drawing speed of the air sucker was adjusted so that the fineness of the filaments obtained at this time may become 3.0 d/f. The collected filament fleece was carried on the endless conveyor at a moving speed of 50 m/min, and introduced between the rolls, pressurized at 80 kg/cm, of a point bond processor comprising an embossing roll and a smooth surface roll which are heated at 141° C. Thus, a filament nonwoven fabric having a basis weight of 30 g/m² was obtained.

In the filament nonwoven fabric obtained, the thermally press bonded portions had a low area rate of 3%. The filament nonwoven fabric exhibited a low tensile strength and poor abrasion resistance.

COMPARATIVE EXAMPLE 2

Polypropylene having a MFR of 50 and a melting point of 160° C. was extruded from a 60 mmφ extruder at an extruding temperature of 220° C. On the other hand, a high density polyethylene having a MI of 25 and a melting point of 133° C. was extruded from another 60 mmφ extruder at an extruding temperature of 220° C. So as to obtain fibers having a cross section with a volume ratio of 5/5 (core component polypropylene/sheath component polyethylene), these resins were spun through a core/sheath type composite spinneret at 2200 cc/min in total amount. As the spinneret, a spinneret having circular spinning holes with a hole diameter of 0.35 mm arranged in 550 holes×5 columns in the longitudinal direction of the spinneret was used. The spinneret was designed so that the cross section of the fibers may become core/sheath type. A group of fibers discharged from the spinneret was introduced into an air sucker and stretched by drawing, so that a group of filaments was obtained. Then, the group of filaments discharged from the air sucker was electrically charged by applying same electric charges with a corona discharge device. Thereafter, it was passed through between a couple of vibrating wing-like tools (flaps) so as to open the filaments. The opened filament group was collected as a filament fleece on an endless conveyor having suckers on its back surface. The drawing speed of the air sucker was adjusted so that the fineness of the filaments obtained at this time may become 2.2 d/f. The collected filament fleece was carried on the endless conveyor at a moving speed of 50 m/min, and introduced between the rolls, pressurized at 80 kg/cm, of a point bond processor comprising an embossing roll and a smooth surface roll which are heated at 130° C. Thus, a filament nonwoven fabric having a basis weight of 27 g/m² was obtained.

In the filament nonwoven fabric obtained, the average value of the distance between adjacent thermally press bonded portions in the direction of the mechanical direction of the nonwoven fabric was large. And the filament nonwoven fabric exhibited a low tensile strength and poor abrasion resistance.

COMPARATIVE EXAMPLE 3

Polypropylene having a MFR of 50 and a melting point of 160° C. was extruded from a 60 mmφ extruder at an extruding temperature of 220° C. On the other hand, a high density polyethylene having a MI of 25 and a melting point of 133° C. was extruded from another 60 mmφ extruder at an extruding temperature of 220° C. So as to obtain fibers having a cross section with a volume ratio of 5/5 (core component polypropylene/sheath component polyethylene), these resins were spun through a core/sheath type composite spinneret at 2200 cc/min in total amount. As the spinneret, a spinneret having circular spinning holes with a hole diameter of 0.35 mm arranged in 550 holes×5 columns in the longitudinal direction of the spinneret was used. The spinneret was designed so that the cross section of the fibers may become core/sheath type. A group of fibers discharged from the spinneret was introduced into an air sucker and stretched by drawing, so that a group of filaments was obtained. Then, the group of filaments discharged from the air sucker was electrically charged by applying same electric charges with a corona discharge device. Thereafter, it was passed through between a couple of vibrating wing-like tools (flaps) so as to open the filaments. The opened filament group was collected as a filament fleece on an endless conveyor having suckers on its back surface. The drawing speed of the air sucker was adjusted so that the fineness of the filaments obtained at this time may become 2.5 d/f. The collected filament fleece was carried on the endless conveyor at a moving speed of 60 m/min, and introduced between the rolls, pressurized at 80 kg/cm, of a point bond processor comprising an embossing roll and a smooth surface roll which are heated at 130° C. Thus, a filament nonwoven fabric having a basis weight of 20 g/m² was obtained.

In the obtained filament nonwoven fabric, the thermally press bonded portions had a high area rate of 30%, and the tensile strength of the nonwoven fabric was high. However, hand feeling of the filament nonwoven fabric was poor.

TABLE 1

| | Filament Nonwoven Fabric | | | | Thermally Press Bonded Portion | | | | | Evaluation of Nonwoven Fabric | | |
|---|---|---|---|---|---|---|---|---|---|---|---|---|
| | Resin | | Type of Conjugation | Fineness | Basic Weight | Area Rate | X | Y | y/x | Shape | Tensile Strength | Hand Feeling | Abrasion Resistance |
| | Core | Sheath | — | d/f | g/m$^2$ | % | mm | mm | — | — | kg/cm/(g/m$^2$) | Point | — |
| Example 1 | PP | PP | Single Fiber | 2.0 | 20 | 15 | 1.0 | 1.5 | 1.5 | Rhombus | 0.040 | 9 | ○ |
| Example 2 | PP | PP | Single Fiber | 2.0 | 20 | 24 | 1.5 | 1.5 | 2.0 | Rhombus | 0.050 | 8 | ○ |
| Example 3 | PP | PE | Core/Sheath | 2.5 | 28 | 13 | 1.3 | 2.0 | 2.0 | Rhombus | 0.038 | 9 | ○ |
| Example 4 | PP | PE | Core/Sheath | 1.5 | 15 | 15 | 1.2 | 1.6 | 3.0 | Elliptic | 0.037 | 10 | ○ |
| Example 5 | PP | PE | Eccentric Core/Sheath | 3.0 | 25 | 21 | 1.6 | 2.0 | 2.8 | Elliptic | 0.041 | 8 | ○ |
| Example 6 | PET | PE | Core/Sheath | 2.7 | 28 | 15 | 1.3 | 1.5 | 4.0 | Rectangular | 0.039 | 9 | ○ |
| Example 7 | PP | coPP | Core/Sheath | 2.0 | 21 | 21 | 1.6 | 2.1 | 2.1 | Rhombus | 0.042 | 7 | ○ |
| Comparative Example 1 | PP | PP | Single Fiber | 3.0 | 30 | 3 | 2.0 | 2.5 | 1.0 | Rhombus | 0.010 | 7 | x |
| Comparative Example 2 | PP | PE | Core/Sheath | 2.2 | 27 | 9 | 2.5 | 3.0 | 1.1 | Elliptic | 0.012 | 8 | x |
| Comparative Example 3 | PP | PE | Core/Sheath | 2.5 | 20 | 30 | 1.0 | 1.0 | 1.5 | Rectangular | 0.055 | 2 | ○ |

PP: polypropylene PE: polyethylene PET: polyethylene terephthalate coPP: propylene-ethylene copolymer (ethylene copolymerization rate of 6 wt. %)

Industrial Applicability (1) The present invention provides a filament nonwoven fabric having thermally press bonded portions, in which drawbacks of conventional filament nonwoven fabrics having thermally press bonded portions are improved. The filament nonwoven fabric of the present invention has a high strength, good hand feeling, and excellent abrasion resistance.

That is, the present invention provides a filament nonwoven fabric comprising thermoplastic fibers with a fineness of 0.1 to 10 d/f, having a basis weight of 5 to 35 g/m$^2$, and having thermally press bonded portions, in which the below mentioned conditions (A), (B), and (C) are satisfied. By satisfying these conditions, a filament nonwoven fabric having a high strength, good hand feeling, and excellent abrasion resistance, in which fuzz or pilling is hardly developed, can be obtained. The conditions (A), (B), and (C) are as follows:

(A) the area rate of the thermally press bonded portions being 5 to 25%;

(B) $X \leq 2.0$ (mm)
  X: the average value of the distance between adjacent thermally press bonded portions in the mechanical direction of the nonwoven fabric;
  $Y \leq 2.5$ (mm)
  Y: the average value of the distance between adjacent thermally press bonded portions in the direction perpendicular to the mechanical direction of the nonwoven fabric; and (C) the average value of the ratio between the maximum diameters of the thermally press bonded portions satisfying $1 \leq y/x \leq 15$, wherein
  x: the average value of the maximum diameter of the thermally press bonded portions in the mechanical direction of the nonwoven fabric; and
  y: the average value of the maximum diameter of the thermally press bonded portions in the direction perpendicular to the mechanical direction of the nonwoven fabric.

(2) In the filament nonwoven fabric of the present invention, it is preferable that the fineness of the thermoplastic fibers that constitutes the nonwoven fabric is from 0.1 to 6 d/f, and that X satisfies (B') $0.3 \leq X \leq 1.6$ (mm).

According to these conditions, a filament nonwoven fabric having a high strength, good hand feeling, and excellent abrasion resistance, in which development of fuzz or pilling is further reduced, can be obtained.

(3) According to a preferable embodiment, a filament nonwoven fabric of the present invention is obtained by the spun bond method. According to this method, a filament nonwoven fabric excellent in strength properties such as tensile strength can be easily obtained. Furthermore, the filament nonwoven fabric obtained by this method has a very excellent productivity, because it is obtainable simply by opening and collecting filaments that are obtained by melt spinning.

(4) In the filament nonwoven fabric of the present invention, it is preferable that the thermoplastic fibers are conjugated fibers comprising a high melting core component and a low melting or softening sheath component, the low melting or softening component having a volume ratio of 40 to 90% based on the total volume of the conjugated fibers. By satisfying these conditions, a thermal press bonding process can be performed at a temperature near the softening or melting point of the sheath component located at the surface of the fibers. Therefore, damage to the core component by heat can be reduced, and a nonwoven fabric with good hand feeling can be obtained. Furthermore, it is more preferable that the proportion of the sheath component is increased, so that the thermally press bonded portions are more firmly fixed and abrasion resistance is more improved.

(5) In the filament nonwoven fabric of the present invention using the above-mentioned core/sheath type conjugated fibers, it is preferable to use polyethylene for the low melting component of the thermoplastic fibers. Accordingly, thermal press bonding process can be performed at a relatively low temperature, so that damage to the core component by heat is small. Thus, a nonwoven fabric with good hand feeling can be obtained.

(6) In the filament nonwoven fabric of the present invention, it is preferable that the low softening or melting component of the thermoplastic fibers comprises at least one selected from olefin binary copolymers and olefin terpolymers. Accordingly, a nonwoven fabric excellent in processability, with which other materials such as polypropylene nonwoven fabrics and films can be easily bonded with heat, can be provided.

(7) In the filament nonwoven fabric of the present invention, it is preferable to use polypropylene for the core component of the thermoplastic fibers. By using this, a relatively soft filament nonwoven fabric can be obtained. Furthermore, in the filament nonwoven fabric of the present invention, it is also preferable to use polyethylene terephthalate for the core component in the thermoplastic components. By using this, a filament nonwoven fabric having a higher strength, which exhibits more excellent elasticity (cushion property) when crimp is developed, can be obtained.

(8) In an absorbent article of the present invention, by using the filament nonwoven fabric of the present invention in a part thereof, absorbent articles having a high strength and good hand feeling, in which fuzz or pilling is hardly developed when used, can be provided.

As described above, the filament nonwoven fabric of the present invention is excellent in abrasion resistance, strength, and hand feeling. Thus, it can be used for various applications such as clothing, industrial materials, materials of construction and architecture, agricultural and horticultural materials, materials of daily needs, medical and sanitary materials, and the like. Particularly, it can be suitably used in absorbent articles such as sanitary napkins and disposable diapers.

We claim:

1. A filament nonwoven fabric comprising thermoplastic fibers with a fineness of 0.1 to 10 d/f, having a basis weight of 5 to 35 g/m$^2$, and having thermally press bonded portions, in which the conditions (A), (B), and (C) below are satisfied:

(A) the area rate of the thermally press bonded portions being from 5 to 25%;

(B) $X \leq 2.0$ (mm)

X: the average value of the distance between adjacent thermally press bonded portions in the mechanical direction of the nonwoven fabric;

$Y \leq 2.5$ (mm)

Y: the average value of the distance between adjacent thermally press bonded portions in the direction perpendicular to the mechanical direction of the nonwoven fabric; and (C) the average value of the ratio between the maximum diameters of the thermally press bonded portions satisfying $1 \leq y/x \leq 15$, wherein x: the average value of the maximum diameter of the thermally press bonded portions in the mechanical direction of the nonwoven fabric; and y: the average value of the maximum diameter of the thermally press bonded portions in the direction perpendicular to the mechanical direction of the nonwoven fabric.

2. A filament nonwoven fabric according to claim 1, wherein the fineness of the thermoplastic fibers that constitute the nonwoven fabric is from 0.1 to 6 d/f, and wherein X satisfies (B') $0.3 \leq X \leq 1.6$ (mm).

3. A filament nonwoven fabric according to claim 1 or 2, wherein the filament nonwoven fabric is one obtained by the spun bond method.

4. A filament nonwoven fabric according to claim 1 or 2, wherein the thermoplastic fibers are conjugated fibers comprising a high melting core component and a low melting or softening sheath component, the low melting or softening component having a volume ratio of 40 to 90% based on the total volume of the conjugated fibers.

5. A filament nonwoven fabric according to claim 4, wherein the low melting component of the thermoplastic fibers comprises polyethylene.

6. A filament nonwoven fabric according to claim 4, wherein the low melting or softening component of the thermoplastic fibers comprises at least one selected from olefin binary copolymers and olefin terpolymers.

7. A filament nonwoven fabric according to claim 4, wherein the core component of the thermoplastic fibers comprises at least one selected from polypropylene and polyethylene terephthalate.

8. An absorbent article using a filament nonwoven fabric according to claim 1 or 2 in a part thereof.

9. A filament nonwoven fabric according to claim 2, wherein the filament nonwoven fabric is one obtained by the spun bond method.

10. A filament nonwoven fabric according to claim 2, wherein the thermoplastic fibers are conjugated fibers comprising a high melting core component and a low melting or softening sheath component, the low melting or softening component having a volume ratio of 40 to 90% based on the total volume of the conjugated fibers.

11. A filament nonwoven fabric according to claim 10, wherein the low melting component of the thermoplastic fibers comprises polyethylene.

12. A filament nonwoven fabric according to claim 10, wherein the low melting or softening component of the thermoplastic fibers comprises at least one selected from olefin binary copolymers and olefin terpolymers.

13. A filament nonwoven fabric according to claim 10, wherein the core component of the thermoplastic fibers comprises at least one selected from polypropylene and polyethylene terephthalate.

14. An absorbent article using a filament nonwoven fabric according to claim 2 in a part thereof.

* * * * *